(12) United States Patent
Boesen et al.

(10) Patent No.: US 10,582,289 B2
(45) Date of Patent: *Mar. 3, 2020

(54) ENHANCED BIOMETRIC CONTROL SYSTEMS FOR DETECTION OF EMERGENCY EVENTS SYSTEM AND METHOD

(71) Applicant: BRAGI GmbH, München (DE)

(72) Inventors: Peter Vincent Boesen, München (DE); Lisa Kingscott, München (DE); Rafael Pereira, München (DE)

(73) Assignee: BRAGI GmbH, München (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/144,436

(22) Filed: Sep. 27, 2018

(65) Prior Publication Data

US 2019/0037299 A1    Jan. 31, 2019

Related U.S. Application Data

(63) Continuation of application No. 15/290,519, filed on Oct. 11, 2016, now Pat. No. 10,104,458.

(Continued)

(51) Int. Cl.
*H04R 1/10* (2006.01)
*A61B 5/024* (2006.01)
(Continued)

(52) U.S. Cl.
CPC .......... *H04R 1/1041* (2013.01); *A61B 5/0008* (2013.01); *A61B 5/02438* (2013.01);
(Continued)

(58) Field of Classification Search
CPC .... H04R 1/1041; H04R 1/105; H04R 1/1016; H04R 2420/07; A61B 5/22; A61B 5/0008; A61B 5/02438; G10K 13/002
(Continued)

(56) References Cited

U.S. PATENT DOCUMENTS 2,325,590 A    8/1943 Carlisle et al.
2,430,229 A    11/1947 Kelsey
(Continued)

FOREIGN PATENT DOCUMENTS

CN    204244472 U    4/2015
CN    104683519 A    6/2015
(Continued)

OTHER PUBLICATIONS

Akkermans, "Acoustic Ear Recognition for Person Identification", Automatic Identification Advanced Technologies, 2005 pp. 219-223.
(Continued)

*Primary Examiner* — William A Jerez Lora
(74) *Attorney, Agent, or Firm* — Goodhue, Coleman & Owens, P.C.

(57) ABSTRACT

A system, method and personal area network for communicating utilizing a wireless earpiece. The wireless earpiece is linked with a communications device. Sensor measurements of a condition of a user are performed utilizing sensors of the wireless earpiece. A determination is made whether the sensor measurements exceed one or more thresholds. Communications regarding the sensor measurements are sent from the wireless earpiece to the communications device regarding the condition of the user.

9 Claims, 3 Drawing Sheets

Related U.S. Application Data

(60) Provisional application No. 62/244,152, filed on Oct. 20, 2015.

(51) Int. Cl.
 *A61B 5/00* (2006.01)
 *A61B 5/22* (2006.01)
 *G01K 13/00* (2006.01)

(52) U.S. Cl.
 CPC .............. *A61B 5/22* (2013.01); *G01K 13/002* (2013.01); *H04R 1/105* (2013.01); *H04R 1/1016* (2013.01); *H04R 2420/07* (2013.01)

(58) Field of Classification Search
 USPC .......................................................... 381/74
 See application file for complete search history.

(56) References Cited

U.S. PATENT DOCUMENTS

| | | |
|---|---|---|
| 3,047,089 A | 7/1962 | Zwislocki |
| D208,784 S | 10/1967 | Sanzone |
| 3,586,794 A | 6/1971 | Michaelis |
| 3,696,377 A | 10/1972 | Wall |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,036,479 A | 7/1991 | Prednis et al. |
| 5,123,016 A | 6/1992 | Muller et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| 5,444,786 A | 8/1995 | Raviv |
| D367,113 S | 2/1996 | Weeks |
| 5,497,339 A | 3/1996 | Bernard |
| 5,513,099 A | 4/1996 | Schein |
| 5,596,587 A | 1/1997 | Douglas et al. |
| 5,606,621 A | 2/1997 | Reiter et al. |
| 5,613,222 A | 3/1997 | Guenther |
| 5,654,530 A | 8/1997 | Sauer et al. |
| 5,689,252 A | 11/1997 | Ayanoglu et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| 5,844,996 A | 12/1998 | Enzmann et al. |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,185,152 B1 | 2/2001 | Shen |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,522,266 B1 | 2/2003 | Soehren et al. |
| 6,542,721 B2 | 4/2003 | Boesen |
| 6,560,468 B1 | 5/2003 | Boesen |
| 6,563,301 B2 | 5/2003 | Gventer |
| 6,654,721 B2 | 11/2003 | Handelman |
| 6,664,713 B2 | 12/2003 | Boesen |
| 6,681,176 B2 | 1/2004 | Funk et al. |
| 6,690,807 B1 | 2/2004 | Meyer |
| 6,694,180 B1 | 2/2004 | Boesen |
| 6,718,043 B1 | 4/2004 | Boesen |
| 6,721,657 B2 | 4/2004 | Ford et al. |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,943,614 B1 | 9/2005 | Kuei |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| 7,279,887 B1 | 10/2007 | King et al. |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| 7,532,901 B1 | 5/2009 | LaFranchise et al. |
| D601,134 S | 9/2009 | Elabidi et al. |
| 7,668,652 B2 | 2/2010 | Spencer et al. |
| 7,825,626 B2 | 11/2010 | Kozisek |
| 7,859,469 B1 | 12/2010 | Rosener et al. |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| 8,238,967 B1 | 8/2012 | Arnold et al. |
| 8,253,589 B2 | 8/2012 | Grimm et al. |
| D666,581 S | 9/2012 | Perez |
| 8,300,864 B2 | 10/2012 | Müllenborn et al. |
| 8,406,448 B2 | 3/2013 | Lin et al. |
| 8,430,817 B1 | 4/2013 | Al-Ali et al. |
| 8,436,780 B2 | 5/2013 | Schantz et al. |
| D687,021 S | 7/2013 | Yuen |

(56) References Cited

U.S. PATENT DOCUMENTS

| | | |
|---|---|---|
| 8,679,012 B1 | 3/2014 | Kayyali |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,229,227 B2 | 1/2016 | Border et al. |
| 9,317,241 B2 | 4/2016 | Tranchina |
| 9,461,403 B2 | 10/2016 | Gao et al. |
| 9,510,159 B1 | 11/2016 | Cuddihy et al. |
| D773,439 S | 12/2016 | Walker |
| D775,158 S | 12/2016 | Dong et al. |
| 9,524,631 B1 | 12/2016 | Agrawal et al. |
| D777,710 S | 1/2017 | Palmborg et al. |
| 9,544,689 B2 | 1/2017 | Fisher et al. |
| D788,079 S | 5/2017 | Son et al. |
| 9,684,778 B2 | 6/2017 | Tharappel et al. |
| 9,711,062 B2 | 7/2017 | Ellis et al. |
| 9,729,979 B2 | 8/2017 | Özden |
| 9,767,709 B2 | 9/2017 | Ellis |
| 9,818,005 B2 | 11/2017 | Yeager et al. |
| 9,821,767 B2 | 11/2017 | Nixon |
| 9,848,257 B2 | 12/2017 | Ambrose et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0079165 A1 | 4/2003 | Ffrench et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0102931 A1 | 5/2004 | Ellis et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0197063 A1 | 9/2005 | White |
| 2005/0212911 A1 | 9/2005 | Marvit et al. |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0159298 A1* | 7/2006 | von Dombrowski .. H04R 25/48 |
| | | 381/330 |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2006/0276987 A1 | 12/2006 | Bolander et al. |
| 2007/0102009 A1 | 5/2007 | Wong et al. |
| 2007/0239225 A1 | 10/2007 | Saringer |
| 2007/0242834 A1 | 10/2007 | Coutinho et al. |
| 2007/0247800 A1 | 10/2007 | Smith et al. |
| 2007/0269785 A1 | 11/2007 | Yamanoi |
| 2008/0013747 A1 | 1/2008 | Tran |
| 2008/0076972 A1 | 3/2008 | Dorogusker et al. |
| 2008/0090622 A1 | 4/2008 | Kim et al. |
| 2008/0102424 A1 | 5/2008 | Holljes |
| 2008/0146890 A1 | 6/2008 | LeBoeuf et al. |
| 2008/0187163 A1 | 8/2008 | Goldstein et al. |
| 2008/0215239 A1 | 9/2008 | Lee |
| 2008/0253583 A1 | 10/2008 | Goldstein et al. |
| 2008/0254780 A1 | 10/2008 | Kuhl et al. |
| 2008/0255430 A1 | 10/2008 | Alexandersson et al. |
| 2008/0267416 A1* | 10/2008 | Goldstein ............ H04R 1/1091 |
| | | 381/56 |
| 2008/0298606 A1 | 12/2008 | Johnson et al. |
| 2008/0318518 A1 | 12/2008 | Coutinho et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0041313 A1 | 2/2009 | Brown |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0182913 A1 | 7/2009 | Rosenblatt et al. |
| 2009/0191920 A1 | 7/2009 | Regen et al. |
| 2009/0226017 A1 | 9/2009 | Abolfathi et al. |
| 2009/0240947 A1 | 9/2009 | Goyal et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2009/0299215 A1 | 12/2009 | Zhang |
| 2009/0303073 A1 | 12/2009 | Gilling et al. |
| 2009/0304210 A1 | 12/2009 | Weisman |
| 2010/0007805 A1 | 1/2010 | Vitito |
| 2010/0033313 A1 | 2/2010 | Keady et al. |
| 2010/0075631 A1 | 3/2010 | Black et al. |
| 2010/0106356 A1 | 4/2010 | Trepagnier et al. |
| 2010/0166206 A1 | 7/2010 | Macours |
| 2010/0168075 A1 | 7/2010 | Dahlstrom et al. |
| 2010/0203831 A1 | 8/2010 | Muth |
| 2010/0207651 A1 | 8/2010 | Suto |
| 2010/0210212 A1 | 8/2010 | Sato |
| 2010/0285771 A1 | 11/2010 | Peabody |
| 2010/0290636 A1 | 11/2010 | Mao et al. |
| 2010/0320961 A1 | 12/2010 | Castillo et al. |
| 2011/0018731 A1 | 1/2011 | Linsky et al. |
| 2011/0102276 A1 | 5/2011 | Jimenez et al. |
| 2011/0103609 A1 | 5/2011 | Pelland et al. |
| 2011/0137141 A1* | 6/2011 | Razoumov ............ A61B 5/0002 |
| | | 600/316 |
| 2011/0140844 A1 | 6/2011 | McGuire et al. |
| 2011/0140956 A1 | 6/2011 | Henry et al. |
| 2011/0239497 A1 | 10/2011 | McGuire et al. |
| 2011/0286615 A1 | 11/2011 | Olodort et al. |
| 2011/0293105 A1 | 12/2011 | Arie et al. |
| 2012/0057740 A1 | 3/2012 | Rosal |
| 2012/0155670 A1 | 6/2012 | Rutschman |
| 2012/0159617 A1 | 6/2012 | Wu et al. |
| 2012/0162891 A1 | 6/2012 | Tranchina et al. |
| 2012/0163626 A1 | 6/2012 | Booij et al. |
| 2012/0197737 A1 | 8/2012 | LeBoeuf et al. |
| 2012/0235883 A1 | 9/2012 | Border et al. |
| 2012/0309453 A1 | 12/2012 | Maguire |
| 2013/0010657 A1* | 1/2013 | Hannosh ............... H04M 9/082 |
| | | 370/280 |
| 2013/0106454 A1 | 5/2013 | Liu et al. |
| 2013/0154826 A1 | 6/2013 | Ratajczyk |
| 2013/0178967 A1 | 7/2013 | Mentz |
| 2013/0200999 A1 | 8/2013 | Spodak et al. |
| 2013/0204617 A1 | 8/2013 | Kuo et al. |
| 2013/0281795 A1 | 10/2013 | Varadan |
| 2013/0293494 A1 | 11/2013 | Reshef |
| 2013/0316642 A1 | 11/2013 | Newham |
| 2013/0316649 A1* | 11/2013 | Newham ............... H04W 88/04 |
| | | 455/41.2 |
| 2013/0343585 A1 | 12/2013 | Bennett et al. |
| 2013/0346168 A1 | 12/2013 | Zhou et al. |

(56) References Cited

U.S. PATENT DOCUMENTS

| | | |
|---|---|---|
| 2014/0002357 A1 | 1/2014 | Pombo et al. |
| 2014/0004912 A1 | 1/2014 | Rajakarunanayake |
| 2014/0010391 A1 | 1/2014 | Ek et al. |
| 2014/0020089 A1 | 1/2014 | Perini, II |
| 2014/0038544 A1* | 2/2014 | Jones .................. G08B 13/196 455/404.2 |
| 2014/0072136 A1 | 3/2014 | Tenenbaum et al. |
| 2014/0072146 A1 | 3/2014 | Itkin et al. |
| 2014/0073429 A1 | 3/2014 | Meneses et al. |
| 2014/0079257 A1 | 3/2014 | Ruwe et al. |
| 2014/0088454 A1* | 3/2014 | Mack ...................... A61B 5/11 600/553 |
| 2014/0106677 A1 | 4/2014 | Altman |
| 2014/0122116 A1 | 5/2014 | Smythe |
| 2014/0146973 A1 | 5/2014 | Liu et al. |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0237518 A1 | 8/2014 | Liu |
| 2014/0270227 A1 | 9/2014 | Swanson |
| 2014/0270271 A1 | 9/2014 | Dehe et al. |
| 2014/0276227 A1 | 9/2014 | Peérez |
| 2014/0279889 A1 | 9/2014 | Luna |
| 2014/0310595 A1 | 10/2014 | Acharya et al. |
| 2014/0321682 A1 | 10/2014 | Kofod-Hansen et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0035680 A1 | 2/2015 | Li et al. |
| 2015/0036835 A1 | 2/2015 | Chen |
| 2015/0056584 A1 | 2/2015 | Boulware et al. |
| 2015/0110587 A1 | 4/2015 | Hori |
| 2015/0124058 A1 | 5/2015 | Okpeva et al. |
| 2015/0148989 A1 | 5/2015 | Cooper et al. |
| 2015/0181356 A1 | 6/2015 | Krystek et al. |
| 2015/0230022 A1 | 8/2015 | Sakai et al. |
| 2015/0245127 A1 | 8/2015 | Shaffer |
| 2015/0256949 A1 | 9/2015 | Vanpoucke et al. |
| 2015/0264472 A1 | 9/2015 | Aase |
| 2015/0264501 A1 | 9/2015 | Hu et al. |
| 2015/0310720 A1 | 10/2015 | Gettings et al. |
| 2015/0317565 A1 | 11/2015 | Li et al. |
| 2015/0358751 A1 | 12/2015 | Deng et al. |
| 2015/0359436 A1 | 12/2015 | Shim et al. |
| 2015/0364058 A1 | 12/2015 | Lagree |
| 2015/0373467 A1 | 12/2015 | Gelter |
| 2015/0373474 A1 | 12/2015 | Kraft et al. |
| 2015/0379251 A1 | 12/2015 | Komaki |
| 2016/0033280 A1 | 2/2016 | Moore et al. |
| 2016/0034249 A1 | 2/2016 | Lee et al. |
| 2016/0071526 A1 | 3/2016 | Wingate et al. |
| 2016/0072558 A1 | 3/2016 | Hirsch et al. |
| 2016/0073189 A1 | 3/2016 | Lindén et al. |
| 2016/0094550 A1 | 3/2016 | Bradley et al. |
| 2016/0100262 A1 | 4/2016 | Inagaki |
| 2016/0119737 A1 | 4/2016 | Mehnert et al. |
| 2016/0124707 A1 | 5/2016 | Ermilov et al. |
| 2016/0125892 A1 | 5/2016 | Bowen et al. |
| 2016/0140870 A1 | 5/2016 | Connor |
| 2016/0142818 A1 | 5/2016 | Park |
| 2016/0162259 A1 | 6/2016 | Zhao et al. |
| 2016/0209691 A1 | 7/2016 | Yang et al. |
| 2016/0226713 A1 | 8/2016 | Dellinger et al. |
| 2016/0253994 A1 | 9/2016 | Panchapagesan et al. |
| 2016/0324478 A1 | 11/2016 | Goldstein |
| 2016/0352818 A1 | 12/2016 | Han et al. |
| 2016/0353196 A1 | 12/2016 | Baker et al. |
| 2016/0360350 A1 | 12/2016 | Watson et al. |
| 2017/0021257 A1 | 1/2017 | Gilbert |
| 2017/0046503 A1 | 2/2017 | Cho et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0061817 A1 | 3/2017 | May |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0065228 A1 | 3/2017 | Hirano |
| 2017/0078780 A1 | 3/2017 | Qian et al. |
| 2017/0078785 A1 | 3/2017 | Qian et al. |
| 2017/0096065 A1 | 4/2017 | Katsuno et al. |
| 2017/0100277 A1 | 4/2017 | Ke |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0119318 A1 | 5/2017 | Shay et al. |
| 2017/0127168 A1 | 5/2017 | Briggs et al. |
| 2017/0131094 A1 | 5/2017 | Kulik |
| 2017/0142511 A1 | 5/2017 | Dennis |
| 2017/0146801 A1 | 5/2017 | Stempora |
| 2017/0150920 A1 | 6/2017 | Chang et al. |
| 2017/0151085 A1 | 6/2017 | Chang et al. |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0164890 A1 | 6/2017 | Leip et al. |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251295 A1 | 8/2017 | Pergament et al. |
| 2017/0251933 A1 | 9/2017 | Braun et al. |
| 2017/0257698 A1 | 9/2017 | Boesen et al. |
| 2017/0258329 A1 | 9/2017 | Marsh |
| 2017/0263236 A1 | 9/2017 | Boesen et al. |
| 2017/0263376 A1 | 9/2017 | Verschueren et al. |
| 2017/0266494 A1 | 9/2017 | Crankson et al. |
| 2017/0273622 A1 | 9/2017 | Boesen |
| 2017/0280257 A1 | 9/2017 | Gordon et al. |
| 2017/0297430 A1 | 10/2017 | Hori et al. |
| 2017/0301337 A1 | 10/2017 | Golani et al. |
| 2017/0361213 A1 | 12/2017 | Goslin et al. |
| 2017/0366233 A1 | 12/2017 | Hviid et al. |
| 2018/0007994 A1 | 1/2018 | Boesen et al. |
| 2018/0008194 A1 | 1/2018 | Boesen |
| 2018/0008198 A1 | 1/2018 | Kingscott |
| 2018/0009447 A1 | 1/2018 | Boesen et al. |
| 2018/0011006 A1 | 1/2018 | Kingscott |
| 2018/0011682 A1 | 1/2018 | Milevski et al. |
| 2018/0011994 A1 | 1/2018 | Boesen |
| 2018/0012228 A1 | 1/2018 | Milevski et al. |
| 2018/0013195 A1 | 1/2018 | Hviid et al. |

(56) References Cited

U.S. PATENT DOCUMENTS

| | | | |
|---|---|---|---|
| 2018/0014102 A1 | 1/2018 | Hirsch et al. |
| 2018/0014103 A1 | 1/2018 | Martin et al. |
| 2018/0014104 A1 | 1/2018 | Boesen et al. |
| 2018/0014107 A1 | 1/2018 | Razouane et al. |
| 2018/0014108 A1 | 1/2018 | Dragicevic et al. |
| 2018/0014109 A1 | 1/2018 | Boesen |
| 2018/0014113 A1 | 1/2018 | Boesen |
| 2018/0014140 A1 | 1/2018 | Milevski et al. |
| 2018/0014436 A1 | 1/2018 | Milevski |
| 2018/0034951 A1 | 2/2018 | Boesen |
| 2018/0040093 A1 | 2/2018 | Boesen |
| 2018/0042501 A1 | 2/2018 | Adi et al. |
| 2018/0056903 A1 | 3/2018 | Mullett |
| 2018/0063626 A1 | 3/2018 | Pong et al. |

FOREIGN PATENT DOCUMENTS

| | | |
|---|---|---|
| CN | 104837094 A | 8/2015 |
| EP | 1469659 A1 | 10/2004 |
| EP | 1017252 A3 | 5/2006 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2008113053 A1 | 9/2008 |
| WO | 2007034371 A3 | 11/2008 |
| WO | 2010099190 A3 | 1/2011 |
| WO | 2011001433 A2 | 1/2011 |
| WO | 2012071127 A1 | 5/2012 |
| WO | 2013134956 A1 | 9/2013 |
| WO | 2014046602 A1 | 3/2014 |
| WO | 2014043179 A3 | 7/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |
| WO | 2016187869 A1 | 12/2016 |

OTHER PUBLICATIONS

Alzahrani et al: "A Multi-Channel Opto-Electronic Sensor to Accurately Monitor Heart Rate against Motion Artefact during Exercise", Sensors, vol. 15, No. 10, Oct. 12, 2015, pp. 25681-25702, XP055334602, DOI: 10.3390/s151025681 the whole document.
Announcing the $3,333,333 Stretch Goal (Feb. 24, 2014), 14 pages.
Ben Coxworth: "Graphene-based ink could enable low-cost, foldable electronics", "Journal of Physical Chemistry Letters", Northwestern University, (May 22, 2013), 7 pages.
Blain: "World's first graphene speaker already superior to Sennheiser MX400", htt://www.gizmag.com/graphene-speaker-beats-sennheiser-mx400/31660, (Apr. 15, 2014), 7 pages.
BMW, "BMW introduces BMW Connected—The personalized digital assistant", "http://bmwblog.com/2016/01/05/bmw-introduces-bmw-connected-the-personalized-digital-assistant", (Jan. 5, 2016), 14 pages.
BRAGI Is On Facebook (2014), 51 pages.
BRAGI Update—Arrival of Prototype Chassis Parts—More People—Awesomeness (May 13, 2014), 8 pages.
BRAGI Update—Chinese New Year, Design Verification, Charging Case, More People, Timeline(Mar. 6, 2015), 18 pages.
BRAGI Update—First Sleeves From Prototype Tool—Software Development Kit (Jun. 5, 2014), 8 pages.
BRAGI Update—Let's Get Ready to Rumble, A Lot to Be Done Over Christmas (Dec. 22, 2014), 18 pages.
BRAGI Update—Memories From April—Update on Progress (Sep. 16, 2014), 15 pages.
BRAGI Update—Memories from May—Update on Progress—Sweet (Oct. 13, 2014), 16 pages.
BRAGI Update—Memories From One Month Before Kickstarter—Update on Progress (Jul. 10, 2014), 17 pages.
BRAGI Update—Memories From the First Month of Kickstarter—Update on Progress (Aug. 1, 2014), 16 pages.
BRAGI Update—Memories From the Second Month of Kickstarter—Update on Progress (Aug. 22, 2014), 16 pages.
BRAGI Update—New People @BRAGI—Prototypes (Jun. 26, 2014), 9 pages.
BRAGI Update—Office Tour, Tour to China, Tour to CES (Dec. 11, 2014), 14 pages.
BRAGI Update—Status on Wireless, Bits and Pieces, Testing-Oh Yeah, Timeline(Apr. 24, 2015), 18 pages.
BRAGI Update—The App Preview, The Charger, The SDK, BRAGI Funding and Chinese New Year (Feb. 11, 2015), 19 pages.
BRAGI Update—What We Did Over Christmas, Las Vegas & CES (Jan. 19, 2014), 21 pages.
BRAGI Update—Years of Development, Moments of Utter Joy and Finishing What We Started(Jun. 5, 2015), 21 pages.
BRAGI Update—Alpha 5 and Back To China, Backer Day, On Track(May 16, 2015), 15 pages.
BRAGI Update—Beta2 Production and Factory Line(Aug. 20, 2015), 16 pages.
BRAGI Update—Certifications, Production, Ramping Up (Nov. 13, 2015), 15 pages.
BRAGI Update—Developer Units Shipping and Status(Oct. 5, 2015), 20 pages.
BRAGI Update—Developer Units Started Shipping and Status (Oct. 19, 2015), 20 pages.
BRAGI Update—Developer Units, Investment, Story and Status(Nov. 2, 2015), 14 pages.
BRAGI Update—Getting Close(Aug. 6, 2015), 20 pages.
BRAGI Update—On Track, Design Verification, How It Works and What's Next(Jul. 15, 2015), 17 pages.
BRAGI Update—On Track, on Track and Gems Overview (Jun. 24, 2015), 19 pages.
BRAGI Update—Status on Wireless, Supply, Timeline and Open House@BRAGI(Apr. 1, 2015), 17 pages.
BRAGI Update—Unpacking Video, Reviews On Audio Perform and Boy Are We Getting Close(Sep. 10, 2015), 15 pages.
Farr, Christina: "iPads in Every Hospital: Apple's Plan to Crack the $3 Trillion Health Care Sector", "https://www.fastcompany.com/3069060/artists-and-scientists-are-teaming-with-businesses-and-non-profits-on-gender-concerns" (Mar. 18, 2017), 9 pages.
Healthcare Risk Management Review, "Nuance updates computer-assisted physician documentation solution" (Oct. 20, 2016), 2 pages.
Hoffman, "How to Use Android Beam to Wirelessly Transfer Content Between Devices", (Feb. 22, 2013), 4 pages.
Hoyt et. al., "Lessons Learned from Implementation of Voice Recognition for Documentation in the Military Electronic Health Record System", The American Health Information Management Association (2017), 8 pages.
Hyundai Motor America, "Hyundai Motor Company Introduces a Health + Mobility Concept for Wellness in Mobility", Fountain Valley, Californa (2017), 3 pages.
International Search Report & Written Opinion, PCT/EP16/70245 (dated Nov. 16, 2016), 10 pages.
International Search Report & Written Opinion, PCT/EP2016/070231 (dated Nov. 18, 2016), 12 pages.
International Search Report & Written Opinion, PCT/EP2016/070247 (dated Nov. 18, 2016), 13 pages.
International Search Report & Written Opinion, PCT/EP2016/07216 (dated Oct. 18, 2016), 13 pages.
International Search Report & Written Opinion, PCT/EP2016/075118 (dated Mar. 7, 2017), 20 pages.
International Search Report and Written Opinion, PCT/EP2016/070228 (dated Jan. 9, 2017), 13 pages.
Jain A et al: "Score normalization in multimodal biometric systems", Pattern Recognition, Elsevier, GB, vol. 38, No. 12, Dec. 31, 2005, pp. 2270-2285, XPO27610849, ISSN: 0031-3203.
Last Push Before The Kickstarter Campaign Ends on Monday 4pm CET (Mar. 28, 2014), 7 pages.
Lovejoy: "Touch ID built into iPhone display one step closer as third-party company announces new tech", "http://9to5mac.com/2015/07/21/virtualhomebutton/" (Jul. 21, 2015), 14 pages.

(56) References Cited

OTHER PUBLICATIONS

Nemanja Paunovic et al, "A methodology for testing complex professional electronic systems", Serbian Journal of Electrical Engineering, vol. 9, No. 1, Feb. 1, 2012, pp. 71-80, XPO55317584, YU.
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014), 6 pages.
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometirics.html", 4 pages (Jul. 28, 2015).
Staab, Wayne J., et al., "A One-Size Disposable Hearing Aid is Introduced", The Hearing Journal 53(4):36-41) Apr. 2000, 4 pages.
Stretchgoal—It's Your Dash (Feb. 14, 2014), 14 pages.
Stretchgoal—The Carrying Case for the Dash (Feb. 12, 2014), 9 pages.
Stretchgoal—Windows Phone Support (Feb. 17, 2014), 17 pages.
The Dash + The Charging Case & the BRAGI News (Feb. 21, 2014), 12 pages.
The Dash—A Word From Our Software, Mechanical and Acoustics Team + An Update (Mar. 11, 2014), 7 pages.
Update From BRAGI—$3,000,000—Yipee (Mar. 22, 2014), 11 pages.
Weisiger; "Conjugated Hyperbilirubinemia", Jan. 5, 2016, 2 pages.
Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).

* cited by examiner

ENHANCED BIOMETRIC CONTROL SYSTEMS FOR DETECTION OF EMERGENCY EVENTS SYSTEM AND METHOD

PRIORITY STATEMENT

This application is a continuation of U.S. Non-Provisional patent application Ser. No. 15/290,519, filed on Oct. 11, 2016 and claims priority to U.S. Provisional Patent Application No. 62/244,152 filed on Oct. 20, 2015 both titled Enhanced Biometric Control Systems for Detection of Emergency Events System and Method all of which are hereby incorporated by reference in their entireties.

BACKGROUND

I. Field of the Disclosure

The illustrative embodiments relate to wireless earpieces. More specifically, but not exclusively, the illustrative embodiments relate to wireless earpieces for monitoring user biometrics and actions.

II. Description of the Art

The growth of wearable devices is increasing exponentially. This growth is fostered by the decreasing size of microprocessors, circuitry boards, chips, and other components. In some cases, wearable devices may obtain biometric data. An important aspect of biometric data is determining user safety, activities, and conditions. In some cases, determining and reporting the user's biometrics and condition may be difficult because of location, position, effects of the user's condition, or user activity.

SUMMARY OF THE DISCLOSURE

One embodiment of the illustrative embodiments provides a system, method and personal area network for communicating with and utilizing a wireless earpiece. The wireless earpiece is linked with a communications device. Sensor measurements of a condition of a user are performed utilizing sensors of the wireless earpiece. A determination is made whether the sensor measurements exceed one or more thresholds. Communications regarding the sensor measurements are sent from the wireless earpiece to the communications device regarding the condition of the user. Another embodiment provides wireless earpieces including a processor and a memory storing a set of instructions. The set of instructions are executed to perform the method described.

Another embodiment provides a wireless earpiece. The wireless earpiece may include a frame for fitting in an ear of a user. The wireless earpiece may also include a logic engine controlling functionality of the wireless earpiece. The wireless earpiece may also have several sensors receiving biometric information from the user. The wireless earpiece may also include a transceiver communicating with at least a wireless device. The number of sensors take sensor measurements of a condition of a user. The logic engine determines whether the sensor measurements exceed one or more thresholds. The transceiver sends communications regarding the sensor measurements from the wireless earpiece to the wireless device.

BRIEF DESCRIPTION OF THE DRAWINGS

Illustrated embodiments of the present invention are described in detail below with reference to the attached drawing figures, which are incorporated by reference herein, and where.

DETAILED DESCRIPTION OF THE DISCLOSURE

The illustrative embodiments provide a system, method, and personal area network for determining a user's condition and associated biometrics. The user's information may then be communicated to one or more additional wireless earpieces, computing, or communications devices. In one embodiment, the wireless earpieces may be part of a personal area network. The wireless earpieces may be utilized to control, communicate, manage, or interact with several other wearable devices, such as smart glasses, helmets, smart glass, watches or wrist bands, chest straps, implants, displays, clothing, or so forth. A personal area network is a network for data transmissions among devices, such as personal computing, communications, camera, vehicles, entertainment, and medical devices. The personal area network may utilize any number of wired, wireless, or hybrid configurations and may be stationary or dynamic. For example, the personal area network may utilize wireless network protocols or standards, such as INSTEON, IrDA, Wireless USB, Bluetooth, Z-Wave, ZigBee, Wi-Fi, ANT+ or other applicable radio frequency signals. In one embodiment, the personal area network may move with the user.

The wireless earpieces may include any number of sensors for receiving user biometrics, such as pulse rate, blood oxygenation, temperature, calories expended, voice and audio output, and orientation (e.g., body, head, etc.). The sensors may also determine the user's location, position, velocity, impact levels, and so forth. The sensors may also receive user input and convert the user input into commands or selections made across the personal devices of the personal area network. For example, the user input detected by the wireless earpieces may include voice commands, head motions, finger taps, finger swipes, motions or gestures, or other user inputs sensed by the wireless earpieces. The user input may be determined and converted into commands sent to one or more external devices, such as a tablet computer, smart phone, or so forth.

Figure 1:
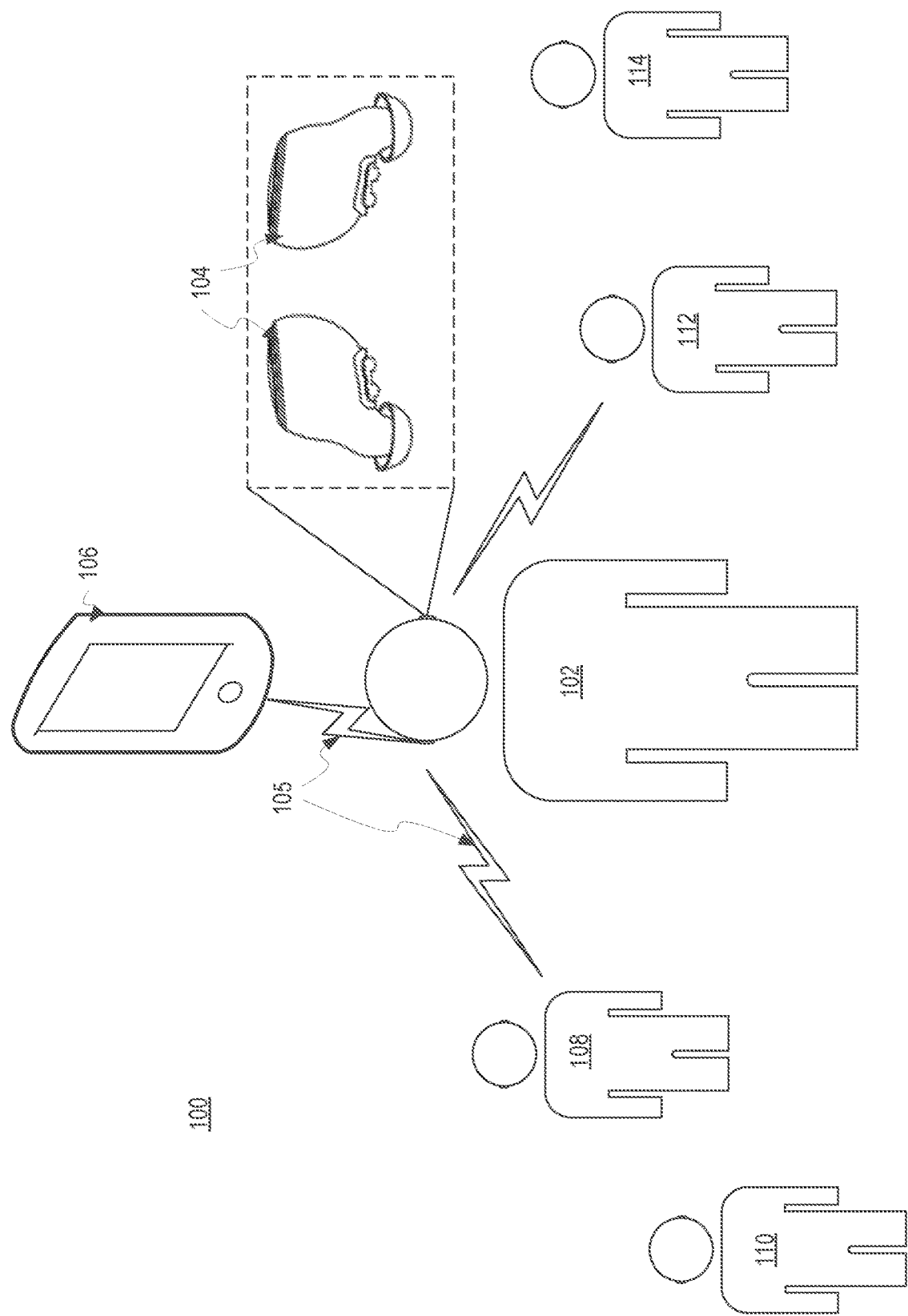
FIG. 1 is a pictorial representation of a communication system in accordance with an illustrative embodiment.

FIG. 1 is a pictorial representation of a communication system 100 in accordance with an illustrative embodiment. In one embodiment, the communication system 100 may represent a personal area network utilized by one or more users. The communication system 100 may also represent any number of systems, environments, or networks in which a user may utilize the described devices and components.

In one embodiment, the communication system 100 may include a user 102 utilizing wireless earpieces 104 and communicating with a communications device 106. The wireless earpieces 104 may communicate with the communications device 106 through a wireless signal 105. The reference to the user 102 may further represent the user utilizing the wireless earpieces 104. Likewise, each of users 108, 110, 112, and 114 may also be utilizing wireless earpieces like the wireless earpieces 104.

The wireless earpieces 104 are shown as worn and separately from their positioning within the ears of the user 102 for purposes of visualization. In one embodiment, the wireless earpieces 104 include a frame shaped to fit substantially within the ear of the user 102. The frame is a support structure partially enclosing and housing the electronic components of the wireless earpieces 104. The frame may include one or more sleeves configured to fit the inside of the ear of the user 102. The sleeves may have extremely tight tolerances to fit user 102. In another embodiment, the sleeves may be custom built. In some applications, temporary adhesives or securing mechanisms (e.g., clamps, straps, extenders, etc.) may be utilized to ensure the wireless earpieces 104 remain in the ears of the user 102 even during the most rigorous and physical activities. For example, the wireless earpieces 104 may be utilized during water polo matches, football games, triathlons, or soccer matches. The wireless earpieces 104 may be configured to play music or audio, receive and make phone calls or other communications, determine ambient environmental conditions (e.g., temperature, altitude, location, speed, heading, etc.), read user biometrics (e.g., heart rate, motion, temperature, sleep, blood oxygenation, voice output, calories burned, forces experienced, etc.), and receive user input, feedback, or instructions.

In one embodiment, the users 102, 108-114 may represent a group, team, or association of individuals participating in a common activity, event, game, or other happening. For example, the users 102, 108-114 may represent teammates. The wireless earpieces 116 utilized by the users 102, 108-114 may be fully enabled or may have partial functionality during the activity. For example, the users 102, 108-114 may be football players and the communications functions of the wireless earpieces 116 may only be activated for a quarterback and a coach of the team (the remaining devices perform sensory operations only and allow sound of the playing environment to be passed through or amplified to the user). The remaining wireless earpieces 116 may be utilized to monitor the users' conditions to ensure their vitals are within satisfactory ranges and any tackles or hits do not result in forces enough to injure or concuss the specific players. Because of the communications system 100, allowed communications may be enhanced while still monitoring the health and safety of the users 102, 108-114.

In another embodiment, the users 102, 108-114 may represent a team working jointly on a project, event, or operation. The users 102, 108-114 may be able to communicate with one another directly or indirectly utilizing the wireless earpieces 116. The communications system 100 may include any number of networks, repeaters, or extenders for extending the range and accessibility of the wireless earpieces. The communications device 106 may receive biometric information for each of the users 102, 108-114 enabling a single person or group too monitor the status and condition of the users 102, 108-114. In other embodiments, the biometric data acquired for the users 102, 108-114 for the corresponding wireless earpieces 116 may be sent remotely to any number of devices or systems. For example, the data may be archived in one or more remote servers and databases for subsequent retrieval through a cloud network and interface. The information reported by the wireless earpieces 116 may be sent to emergency medical services, relatives of each of the users 102, 108-114, or other designated contacts. For example, a potentially dangerous impact detected by the wireless earpieces 104 for the user 102 may be reported to a coach utilizing the communications device 106 as well as the parents or designated guardians of the user 102.

The wireless earpieces 116 may be utilized for early detection and treatment of the users 102, 108-114 based on an injury (e.g., head strike, hit, crash, accident, fall, etc.) or other detected health event (e.g., overheating, hypothermia, heart attack, stroke, seizure, asthma attack, electrocution, etc.). The wireless earpieces 116 may also detect a sound pattern or audio, such as a user groaning, screaming, or other audio event associated with a potential injury or health event. The wireless earpieces 116 may include a library stored within their respective memories including one or more thresholds or data, for determining whether the user may be experiencing an injury or health event.

The devices of the communication system 100 may include any number of devices, components, or so forth communicating with each other directly or indirectly through a wireless (or wired) connection, signal, or link, such as the wireless signals 105. The communications system 100 may be a network and may include any number of network components and devices, such as routers, servers, signal extenders, intelligent network devices, computing devices, or so forth. In one embodiment, the network of the communications system 100 represents a personal area network as previously disclosed. Communications, such as the wireless signals 105, within the communication system 100 may occur through the network or may occur directly between devices, such as the wireless earpieces 104 and the communications device 106 (e.g., direct communication of the wireless signal 105) or between the wireless earpieces 102 and the wireless device 128 (indirect communication through a Wi-Fi network utilizing the wireless signal 105). In one embodiment, the communications system 100 may communicate with or include a wireless network, such as a Wi-Fi, cellular (e.g., 3G, 4G, 5G, PCS, GSM, etc.), Bluetooth, or other radio frequency network. The communications system 100 may also communicate with any number of hard-wired networks, such as local area networks, coaxial networks, fiber-optic networks, or so forth. Communications within the communication system 100 may be operated by one or more users, service providers, or network providers.

As noted, both the wireless earpieces 116 as well as wearable or implantable devices utilized by the users 102, 108-114 may include several sensors including touch sensors, optical sensors, pulse oximeters, microphones, accelerometers, gyroscopes, global positioning chips, and so forth for detecting the biometrics, motion, location, and activities of the user. The information may be utilized to coordinate the audio, video, text, and graphical information presented to the user 116 (as well as the communications device 106) by the respective wireless earpieces 116. In one embodiment, the user 102 may program the wireless earpieces 104 to perform specific activities in response to a specific biometric reading, user motion, command or audio signal, or other action. For example, the user 102 may configure the wireless earpieces 102 (directly or indirectly through a user interface of a computing device communicating with the wireless earpieces 104) to send a concussion alert in response to sensing forces above a specified level applied to the head of the user 102.

Any number of user and environmental conditions may be utilized to generate alerts or other communications. The alerts may also be played audibly to the users 102, 108-114. For example, the user may be played an alert indicating "you may be overheating, consider drinking water and taking a break", or "you just experienced a significant jolt, do you have a concussion?" The wireless earpieces 116 as well as the communications device 106 may include logic for automatically calling emergency services in response to events, such as the user's 102, pulse stopping or slowing significantly. As a result, the communication system 100 may be adapted to the needs and desires of the user 101.

In one embodiment, the communications device 106 may utilize short-range or long-range wireless communications to communicate with the wireless earpieces 116 through the wireless signal 105 or devices of the communications system 100 through the wireless signal 105. For example, the communications device 106 may include a Bluetooth and cellular transceiver within the embedded logical components. For example, the wireless signal 106 may be a Bluetooth, Wi-Fi, Zigbee, Ant+, or other short-range wireless communication.

The communications device 106 may represent any number of wireless or wired electronic communications or computing devices, such as smart phones, laptops, desktop computers, control systems, tablets, displays, gaming devices, music players, personal digital assistants, vehicle systems, or so forth. The communications device 106 may communicate utilizing any number of wireless connections, standards, or protocols (e.g., near field communications, Bluetooth, Wi-Fi, wireless Ethernet, etc.). For example, the communications device 106 may be a touch screen cellular phone communicating with the wireless earpieces 116 utilizing Bluetooth communications. The communications device 106 may implement and utilize any number of operating systems, kernels, instructions, or applications making use of the sensor data or user input received from the wireless earpieces 116. For example, the communications device 106 may represent any number of android, iOS, Windows, open platforms, or other systems. Similarly, the communications device 106 or the wireless earpieces 116 may include several applications utilizing the user input, biometric data, and other feedback from the wireless earpieces 116 to display applicable information and data, control the applications, play audible or tactile alerts, or make other selections. For example, biometric information (including, high, low, average, or other values) may be processed by the wireless earpieces 116 or the communications device 106 to display experienced forces, heart rate, blood oxygenation, altitude, speed, distance traveled, calories burned, or other applicable information.

In one embodiment, the wireless device 106 may include any number of input components and sensors (e.g., like those described regarding the wireless earpieces 116) utilized to augment the input and sensor readings of the wireless earpieces 116. For example, a microphone of the wireless device 106 may determine an amount and type of ambient noise. The noise may be analyzed and utilized to filter the sensor readings made by the wireless earpieces 116 to maximize the accuracy and relevance of the sensor measurements of the wireless earpieces 116. For example, the wireless earpieces 116 may adjust the microphone sensitivity or filter out background noise based on measurements performed by the communications device 106. Filtering, tuning, and adaptation for the sensor measurements may be made for signal noise, electronic noise, or acoustic noise, all of which are applicable in the communication system 100. Sensor measurements made by either the wireless earpieces 116 or communications device 106 may be communicated with one another in the communication system 100. As noted, the communications device 106 is representative of any number of personal computing, communications, exercise, medical, or entertainment devices communicating with the wireless earpieces 116.

With respect to the wireless earpieces 116, sensor measurements or user input may refer to measurements made by one or both wireless earpieces 116 in a set. For example, the right wireless earpieces 104 may determine the user may have experienced a concussive event even though the event was not detected by the left wireless earpiece 104. The wireless earpieces 104 may also switch back and forth between sensors of the left and right wireless earpieces 104 in response to varying noise, errors, or more accurate signals for both wireless earpieces 104. As a result, the clearest sensor signal may be utilized at any given time. In one embodiment, the wireless earpieces 104 may switch sensor measurements in response to the sensor measurements exceeding or dropping below a specified threshold.

The user 102 may also be wearing or carrying any number of sensor-enabled devices, such as heart rate monitors, pacemakers, smart glasses, smart watches or bracelets (e.g., Apple Watch®, Fitbit®, etc.), or other sensory devices worn, attached to, or integrated with the user 102. The data and information from the external sensor devices may be communicated to the wireless earpieces 104. In another embodiment, the data and information from the external sensor devices may be utilized to perform additional processing of the information sent from the wireless earpieces 104 to the communications device 106.

The sensors of the wireless earpieces 104 may be positioned at enantiomeric locations. For example, several colored light emitting diodes may be positioned to provide variable data and information, such as heart rate, respiratory rate, and so forth. The data gathered by the LED arrays may be sampled and used alone or in aggregate with other sensors. As a result, sensor readings may be enhanced and strengthened with additional data.

In another embodiment, the wireless earpieces 102 may represent or communicate with other wireless devices ingested or implanted into a user. For example, the described electronics may be endoscopic pills, pacemakers, tracking devices, contact lenses, oral implants, bone implants, artificial organs, or so forth.

Figure 2:
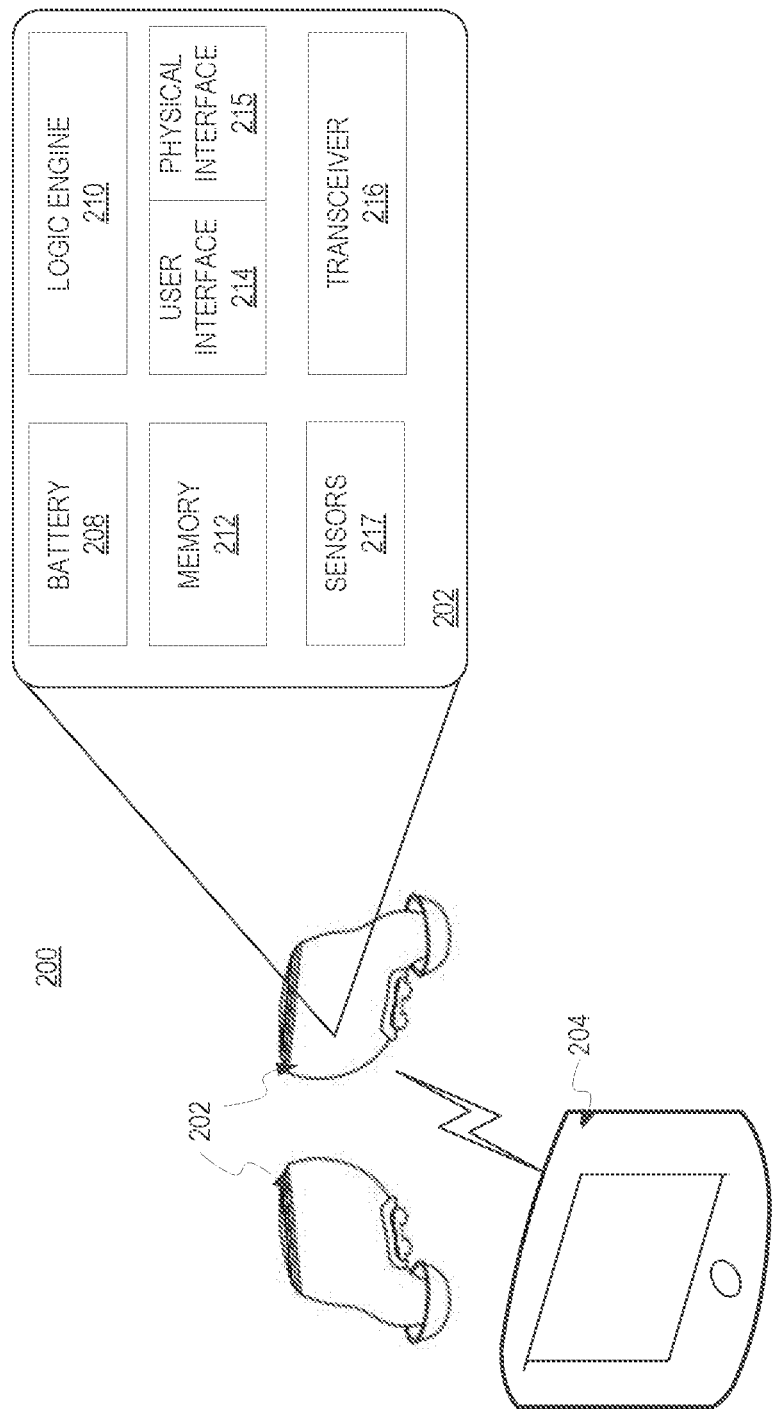
FIG. 2 is a block diagram of wireless earpieces in accordance with an illustrative embodiment.

FIG. 2 is a block diagram of a wireless earpiece system 200 in accordance with an illustrative embodiment. In one embodiment, the wireless earpiece system 200 may include wireless earpieces 202 (described collectively rather than individually). In one embodiment, the wireless earpiece system 200 may enhance communications and functionality of the wireless earpieces 202.

As shown, the wireless earpieces 202 may be wirelessly linked to a computing device 204. For example, the computing device 204 may represent a wireless tablet computer. User input and commands may be received from either the wireless earpieces 202 or the computing device 204 for implementation on either of the devices of the wireless earpiece system 200 (or other externally connected devices). As previously noted, the wireless earpieces 102 may be referred to or described herein as a pair (wireless earpieces) or singularly (wireless earpiece). The description may also refer to components and functionality of each of the wireless earpieces 202 collectively or individually.

In some embodiments, the computing device 204 may act as a logging tool for receiving information, data, or measurements made by the wireless earpieces 202. For example, the computing device 204 may download data from the wireless earpieces 202 in real-time. As a result, the computing device 204 may be utilized to store, display, and synchronize data for the wireless earpieces 202. For example, the computing device 204 may display pulse, oxygenation, distance, calories burned, and so forth as measured by the wireless earpieces 202. The computing device 204 may be configured to receive and display alerts indicating a specific health event or condition has been met. For example, if the forces applied to the sensors 217 (e.g., accelerometers) indicates the user may have experienced a concussion or serious trauma, the wireless earpieces 202 may generate and send a message to the computing device 204. The wireless earpieces 202 and the computing device 204 may have any number of electrical configurations, shapes, and colors and may include various circuitry, connections, and other components.

In one embodiment, the wireless earpieces 202 may include a battery 208, a logic engine 210, a memory 212, a user interface 214, a physical interface 215, a transceiver 216, and sensors 217. The computing device 204 may have any number of configurations and include components and features as are known in the art.

The battery 208 is a power storage device configured to power the wireless earpieces 202. Likewise, the battery 218 is a power storage device configured to power the computing device 204. In other embodiments, the battery 208 may represent a fuel cell, thermal electric generator, piezo electric charger, solar charger, ultra-capacitor, or other existing or developing power storage technologies.

The logic engine 210 is the logic controlling the operation and functionality of the wireless earpieces 202. The logic engine 210 may include circuitry, chips, and other digital logic. The logic engine 210 may also include programs and scripts implemented to operate the logic engine 210. The logic engine 210 may represent hardware, software, firmware, or any combination thereof. In one embodiment, the logic engine 210 may include one or more processors. The logic engine 210 may also represent an application specific integrated circuit (ASIC) or field programmable gate array (FPGA). The logic engine 210 may utilize information from the sensors 212 to determine the biometric information, data, and readings of the user. The logic engine 202 may utilize this information and other criteria to inform the user of the biometrics (e.g., audibly, through an application of a connected device, tactilely, etc.) as well as communicate with the computing device 204 through the transceiver 216.

The logic engine 210 may also process user input to determine commands implemented by the wireless earpieces 202 or sent to the wireless earpieces 204 through the transceiver 216. Specific actions may be associated with biometric data thresholds. For example, the logic engine 210 may implement a macro allowing the user to associate biometric data as sensed by the sensors 217 with specified commands, alerts, and so forth. For example, if the temperature of the user is above or below high and low thresholds, an audible alert may be played to the user and a communication sent to the computing device 204.

In one embodiment, a processor included in the logic engine 210 is circuitry or logic enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks.

The memory 212 is a hardware element, device, or recording media configured to store data or instructions for subsequent retrieval or access later. The memory 212 may represent static or dynamic memory. The memory 212 may include a hard disk, random access memory, cache, removable media drive, mass storage, or configuration suitable as storage for data, instructions, and information. In one embodiment, the memory 212 and the logic engine 210 may be integrated. The memory may use any type of volatile or non-volatile storage techniques and mediums. The memory 212 may store information related to the status of a user, wireless earpieces 202, computing device 204, and other peripherals, such as a wireless device, smart glasses, smart watch, smart case for the wireless earpieces 202, wearable device, and so forth. In one embodiment, the memory 212 may display instructions, programs, drivers, or an operating system for controlling the user interface 214 including one or more LEDs or other light emitting components, speakers, tactile generators (e.g., vibrator), and so forth. The memory 212 may also store the thresholds, conditions, or biometric data (e.g., biometric and data library) associated with biometric events.

The transceiver 216 is a component comprising both a transmitter and receiver which may be combined and share common circuitry on a single housing. The transceiver 216 may communicate utilizing Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols, or communications. The transceiver 216 may also be a hybrid transceiver supporting several different communications. For example, the transceiver 216 may communicate with the computing device 204 or other systems utilizing wired interfaces (e.g., wires, traces, etc.), NFC or Bluetooth communications.

The components of the wireless earpieces 202 may be electrically connected utilizing any number of wires, contact points, leads, busses, wireless interfaces, or so forth. In addition, the wireless earpieces 202 may include any number of computing and communications components, devices or elements which may include busses, motherboards, circuits, chips, sensors, ports, interfaces, cards, converters, adapters, connections, transceivers, displays, antennas, and other similar components.

The physical interface 215 is hardware interface of the wireless earpieces 202 for connecting and communicating with the computing device 204 or other electrical components, devices, or systems.

The physical interface 215 may include any number of pins, arms, or connectors for electrically interfacing with the contacts or other interface components of external devices or other charging or synchronization devices. For example, the physical interface 215 may be a micro USB port. In one embodiment, the physical interface 215 is a magnetic interface automatically couples to contacts or an interface of the computing device 204. In another embodiment, the physical interface 215 may include a wireless inductor for charging the wireless earpieces 202 without a physical connection to a charging device.

The user interface 214 is a hardware interface for receiving commands, instructions, or input through the touch (haptics) of the user, voice commands, or predefined motions. The user interface 214 may be utilized to control the other functions of the wireless earpieces 202. The user interface 214 may include the LED array, one or more touch sensitive buttons or portions, a miniature screen or display, or other input/output components. The user interface 214 may be controlled by the user or based on commands received from the computing device 204 or a linked wireless device.

In one embodiment, the user may provide feedback by tapping the user interface 214 once, twice, three times, or any number of times. Similarly, a swiping motion may be utilized across or in front of the user interface 214 (e.g., the exterior surface of the wireless earpieces 202) to implement a predefined action. Swiping motions in any number of directions or gestures may be associated with specific activities, such as play music, pause, fast forward, rewind, activate a digital assistant (e.g., Siri, Cortana, smart assistant, etc.). The swiping motions may also be utilized to control actions and functionality of the computing device 204 or other external devices (e.g., smart television, camera array, smart watch, etc.). The user may also provide user input by moving his head in a direction or motion or based on the user's position or location. For example, the user may utilize voice commands, head gestures, or touch commands to change the content displayed by the computing device 204.

The sensors 217 may include pulse oximeters, accelerometers, gyroscopes, magnetometers, inertial sensors, photo detectors, miniature cameras, and other similar instruments for detecting location, forces or impact, orientation, motion, and so forth. The sensors 217 may also be utilized to gather optical images, data, and measurements and determine an acoustic noise level, electronic noise in the environment, ambient conditions, and so forth. The sensors 217 may provide measurements or data utilized to filter or select images for display by the computing device 204. For example, motion or sound detected on the left side of the user may be utilized to command the computing device 204 to display camera images from the left side of the user. Motion or sound may be utilized; however, any number of triggers may be utilized to send commands to the computing device 204.

The computing device 204 may include components similar in structure and functionality to those shown for the wireless earpieces 202. The computing device may include any number of processors, batteries, memories, busses, motherboards, chips, transceivers, peripherals, sensors, displays, cards, ports, adapters, interconnects, and so forth. In one embodiment, the computing device 204 may include one or more processors and memories for storing instructions. The instructions may be executed as part of an operating system, application, browser, or so forth to implement the features herein described. In one embodiment, the wireless earpieces 202 may be magnetically or physically coupled to the computing device 204 to be recharged or synchronized or to be stored.

In another embodiment, the computing device 204 may also include sensors for detecting the location, orientation, and proximity of the wireless earpieces 202. For example, the computing device 204 may include optical sensors or cameras for capturing images and other content. When providing sensor information, the wireless earpieces 202 may utilize and detect any number of wavelengths and spectra to provide distinct images, enhancement, data, and biometrics of the user.

As originally packaged, the wireless earpieces 202 and the computing device 204 may include peripheral devices such as charging cords, power adapters, inductive charging adapters, solar cells, batteries, lanyards, additional light arrays, speakers, smart case covers, transceivers (e.g., Wi-Fi, cellular, etc.), or so forth.

Figure 3:
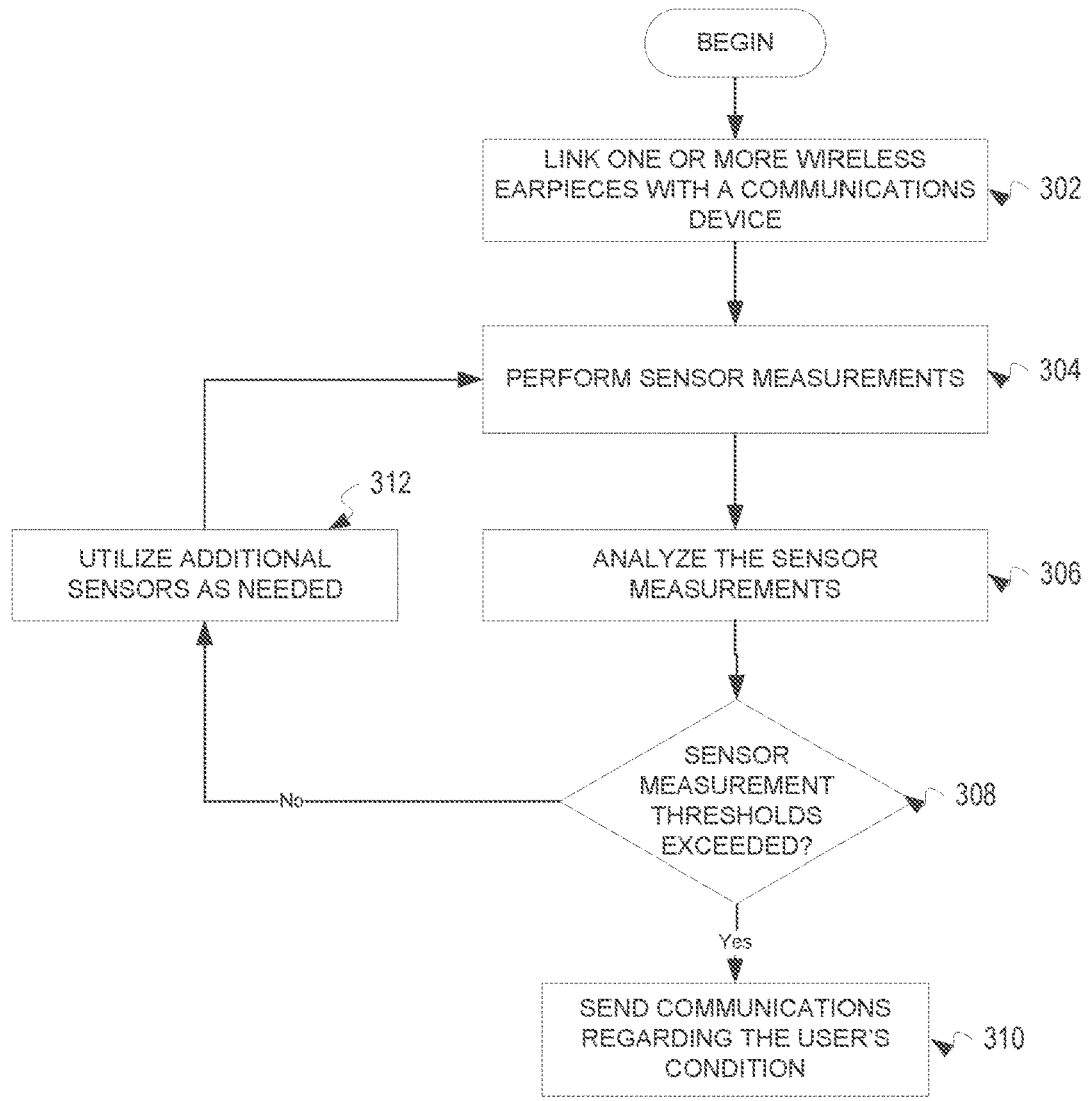
FIG. 3 is a flowchart of a process for determining users conditions utilizing wireless earpieces in accordance with an illustrative embodiment.

FIG. 3 is a flowchart of a process for determining users' conditions utilizing wireless earpieces in accordance with an illustrative embodiment. The process of FIG. 3 may be implemented by one or more wireless earpieces, wearable devices, and any number of other devices communicating directly or through a personal area network.

In one embodiment, the process of FIG. 3 may begin by linking one or more wireless earpieces with a communications device (step 302). The wireless earpieces may be linked with the smart glasses utilizing any number of communications, standards, or protocols. For example, the devices may be linked by a Bluetooth connection. The process may require the devices be paired utilizing an identifier, such as a passcode, password, serial number, voice identifier, radio frequency, or so forth. The wireless earpieces may be linked with the communications device and any number of other devices directly or through a network, such as a personal area network.

Next, the wireless earpieces perform sensor measurements (step 304). The sensor measurements may include performing any number of measurements. The measurements may be performed utilizing a predefined sampling rate (e.g., 1 second, 100 ms, etc.). The measurements may also be triggered in response to specific detected events, such as change in user orientation or position (e.g., change from vertical to horizontal position), changes in velocity (e.g., extreme starts, stops, accelerations, etc.), high forces (e.g., impacts, jolts, etc.), or detected events from other sensors worn by the user.

Next, the wireless earpieces analyze the sensor measurements (step 306). The sensor measurements may be processed or otherwise evaluated by the wireless earpieces. For example, one or more processors of the wireless earpieces may process the incoming data measurements. The sensor measurements are processed for subsequent analysis, determinations, or decisions, implemented by the wireless earpieces.

Next, the wireless earpieces determine whether sensor measurement thresholds are exceeded (step 308). The wireless earpieces may include any number of thresholds, including, high and low thresholds for measurements, such as forces experienced by the user, acceleration, temperature, pulse rate, blood oxygenation, and so forth.

In response to determining the sensor measurement thresholds are exceeded in step 308, the wireless earpieces send communications regarding the user's condition (step 310). In one embodiment, the communications are sent to the communications device linked with the wireless earpieces. For example, the communications may be an alert, status update, warning, or other similar information. In one embodiment, the communication may be an alert indicating the user may have experienced a concussion. Likewise, the communication may indicate the user's temperature has exceeded a threshold and may be experiencing overheating. The information from the wireless earpieces may be particularly valuable for users, such as athletes playing, practicing, or competing in extreme events, conditions, or other settings. For example, the wireless earpieces may be utilized to ensure high school football players in heat prone areas do not overexert themselves, possibly resulting in heat stroke. The communications device may be monitored by team personnel, referees, or umpires, health services groups, parents, or other monitoring groups to ensure the safety of the user.

In response to determining the sensor measurement thresholds are not exceeded in step 308, the wireless earpieces utilize additional sensors as needed (step 312). Additional sensors may be worn or integrated with the user. For example, additional measurements may be taken by a smart watch, or chest strap worn by the user. In another example, a pacemaker of the user may provide additional data regarding pulse, heart rhythm, and other applicable or measured information.

The illustrative embodiments provide a system, method, personal area network, and wireless earpieces for communicating sensor measurements to one or more externally connected devices. The sensor measurements are utilized to send communications, updates, alerts, or other information relative to the condition of the user as well as the user's environment. In one embodiment, the sensor measurements may be utilized to protect the user based on one or more sensor measurements made, such as potential head trauma, overheating, dropping body temperature, low blood oxygenation, excessive or low heart rate, or other applicable information determined by the sensors of the wireless earpieces.

The features, steps, and components of the illustrative embodiments may be combined in any number of ways and are not limited specifically to those described. The illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated other alternatives or exemplary aspects are considered included in the disclosure. The description is merely examples of embodiments, processes or methods of the invention. It is understood any other modifications, substitutions, and/or additions may be made, which are within the intended spirit and scope of the disclosure. For the foregoing, it can be seen the disclosure accomplishes at least all the intended objectives.

The previous detailed description is of a small number of embodiments for implementing the invention and is not intended to be limiting in scope. The following claims set forth several the embodiments of the invention disclosed with greater particularity.

What is claimed is:

1. A method for detection of emergency events, the method comprising the following steps:
    linking a wireless earpiece, having a housing shaped to fit substantially within the ear of a user, with a communications device using a wireless transceiver disposed within the wireless earpiece housing;
    performing sensor measurements of a user utilizing sensors of the wireless earpiece, the sensors disposed within the housing, and wherein the sensors include an inertial sensor for sensing inertial measurements and at least one biometric sensor for sensing biometric measurements;
    analyzing the sensor measurements with a processor operatively connected to the sensors within the wireless earpiece;
    determining at the processor whether any of the sensor measurements exceed one or more thresholds associated with an emergency event;
    communicating an alert to the communications device, if the one or more thresholds associated with an emergency event are exceeded, indicating a possible emergency event; and
    performing wearable sensor measurements of the user using one or more sensors of a wearable device other than the wireless earpiece and communicating the wearable sensor measurements to the wireless earpiece, if the one or more thresholds associated with an emergency event are not exceeded;
    analyzing the wearable sensor measurements with the wireless earpiece processor;
    determining at the processor whether any of the wearable sensor measurements exceed one or more thresholds associated with an emergency event;
    communicating an alert to the communications device, if the one or more thresholds associated with an emergency event are exceeded, indicating a possible emergency event;
    performing environmental sensor measurements of an environment of the user, wherein the environmental sensor measurements include environmental audio sensed with a microphone of the wireless earpiece, if the one or more thresholds associated with an emergency event are not exceeded;
    logging the user sensor measurements, the wearable sensor measurements, and the environmental sensor measurements for subsequent review to a memory disposed within the housing of the wireless earpiece.

2. The method of claim 1, wherein the wearable device other than the wireless earpiece is a second wireless earpiece.

3. The method of claim 1, further comprising the step of communicating with a plurality of users utilizing a plurality of wireless earpieces from the wireless earpiece.

4. The method of claim 1, wherein the wireless earpiece is linked with the communications device utilizing a BLUETOOTH connection.

5. The method of claim 1, wherein the wireless earpiece is one of a plurality of wireless earpieces communicate with the communications device to send communications regarding the condition of each of a plurality of users associated with each of the plurality of wireless earpieces.

6. A method for enhanced biometric detection of emergency events utilizing a wireless earpiece the wireless earpiece comprising:
    a housing shaped to fit substantially within the ear of a user,
    a processor located within the housing;
    a transceiver operatively connected to the processor; and
    a plurality of sensors located on and within the housing and operatively connected to the processor;
    the method comprising the following steps:
    linking, with the transceiver, the wireless earpiece to a communications device;
    performing sensor measurements of the user utilizing the plurality of sensors of the wireless earpiece;
    processing the sensor measurements to determine if the emergency event is occurring;
    communicating an alert through the transceiver to the communications device indicating the user is possibly suffering the emergency event;
    performing wearable sensor measurements of the user using one or more sensors of a wearable device other than the wireless earpiece and communicating the wearable sensor measurements to the wireless earpiece if the emergency event is not occurring;
    processing the wearable sensor measurements to determine if the emergency event is occurring;
    communicating an alert through the transceiver to the communications device indicating the user is possibly suffering the emergency event based upon the wearable sensor measurements;
    performing environmental sensor measurements of an environment of the user;
    processing the environmental sensor measurements to determine if the emergency event is occurring;
    communicating an alert through the transceiver to the communications device indicating the user is possibly suffering the emergency event based upon the environmental sensor measurements; and
    logging the user sensor measurements, the wearable sensor measurements, and the environmental sensor measurements for subsequent review to a memory disposed within the housing of the wireless earpiece.

7. The method of claim 1, wherein the wireless earpiece is one of a plurality of wireless earpieces which communicate with the communications device to send communications regarding the condition of each of a plurality of users associated with each of the plurality of wireless earpieces.

8. The method of claim 7, wherein the plurality of users are engaged in an activity together.

9. The method of claim 1, wherein the wireless earpiece includes a sleeve for maintaining the wireless earpiece in the ear of the user.

\* \* \* \* \*